US011624055B2

(12) United States Patent
Overgaard

(10) Patent No.: US 11,624,055 B2
(45) Date of Patent: Apr. 11, 2023

(54) ISOLATION OF CELLS FROM HATCHED REPTILE EGGS FOR USE IN PRODUCTION OF BIOARTIFICIAL SKIN AND LEATHER

(71) Applicant: Bettina C. Overgaard, Bioggio (CH)

(72) Inventor: Bettina C. Overgaard, Bioggio (CH)

( * ) Notice: Subject to any disclaimer, the term of this patent is extended or adjusted under 35 U.S.C. 154(b) by 319 days.

(21) Appl. No.: 16/603,162

(22) PCT Filed: Apr. 5, 2018

(86) PCT No.: PCT/EP2018/058782
§ 371 (c)(1),
(2) Date: Oct. 4, 2019

(87) PCT Pub. No.: WO2018/185246
PCT Pub. Date: Oct. 11, 2018

(65) Prior Publication Data
US 2020/0032206 A1 Jan. 30, 2020

(30) Foreign Application Priority Data
Apr. 7, 2017 (DK) .......................... PA 2017 00241

(51) Int. Cl.
*C12N 5/071* (2010.01)
*C12N 5/073* (2010.01)
*C12N 5/077* (2010.01)
*C12N 5/0775* (2010.01)
*C14C 13/00* (2006.01)

(52) U.S. Cl.
CPC ......... *C12N 5/0626* (2013.01); *C12N 5/0605* (2013.01); *C12N 5/0656* (2013.01); *C12N 5/0668* (2013.01); *C14C 13/00* (2013.01)

(58) Field of Classification Search
None
See application file for complete search history.

(56) References Cited

U.S. PATENT DOCUMENTS

2016/0097109 A1    4/2016   Forgacs et al.

OTHER PUBLICATIONS

Moore et al., Methods in Cell Science 19: 161-168 (1997) (Year: 1997).*
Cruze et al., Biology of Reproduction (2012) 87(3): 71, 1-11 (Year: 2012).*
Kendall et al., Frontiers in Pharmacology, May 2014, vol. 5, Article 123, pp. 1-13 (Year: 2014).*
Thermo Fisher Growth Factor in Thermo Scientific HyClone Cell Culture Serum, retrieved from the internet:https://static.thermoscientific.com/images/D22225~.pdf (Year: 2022).*
Walmsley et al., Journal of Visualized Experiments, Jan. 2016, 107, e53430, pp. 1-5 (Year: 2016).*
Webb et al., Environ. Sci. Technol. 2014, 48, 14728-14737 (Year: 2014).*
Llames et al., Tissue Engineering Part B: Reviews, vol. 21, No. 4, 2015; pp. 345-353 (Year: 2015).*
Glazkova et al., Veterinary Practice News, Jul. 2015, pp. 34-35 (Year: 2015).*
Kjelland et al., "Feathers and post-hatch eggshells: sources of fibroblast cells for conserving genetic diversity," *Avian Biology Research* 5(3): 123-130, 2012.
Polazzi et al., "Cell culture from lizard skin: A tool for the study of epidermal differentiation," *Tissue and Cell* 43:350-358, 2011.

* cited by examiner

*Primary Examiner* — Evelyn Y Pyla
(74) *Attorney, Agent, or Firm* — Seed IP Law Group LLP

(57) ABSTRACT

The present disclosure relates to a method of generating bioartificial reptile leather by in vitro culturing of isolated cells the chorioallantois of hatched reptile eggs. The disclosure allows production of reptile leather without the ethical issues of conventional reptile farming and the trapping and killing of reptiles for their skin. Furthermore the disclosure allows production of reptile leather from species that are not abundantly available as skin products, such as from endangered species.

27 Claims, 3 Drawing Sheets

ISOLATION OF CELLS FROM HATCHED REPTILE EGGS FOR USE IN PRODUCTION OF BIOARTIFICIAL SKIN AND LEATHER

FIELD OF DISCLOSURE

The present disclosure relates to a method of isolating cells from already hatched reptile eggs for use in production of bioartificial skin and leather. The disclosure allows for isolation of cells for the production of reptile leather and leather without the ethical issues of conventional reptile farming and the trapping and killing of wildlife for their skins. The disclosure also allows isolation of cells for production of leather from species that are not abundantly available as products, such as reptile leather from endangered species. Furthermore, the isolated cells can be used to reduce the waste of leather due to scar tissue formation in farmed animals by using the cells for tissue regeneration which might lead to less animals used in traditional farming. The method of isolating cells from already hatched eggs means that no negative impact will be imposed on animals as opposed to e.g. biopsies taken for the same purpose.

BACKGROUND OF DISCLOSURE

The use of leather by humans for e.g. clothing has been around for thousands of years. There are, however, many ethical issues involved in the use of leather obtained from either conventional reptile farming or from the trapping and killing of wildlife. The conventional reptile farming is often taking place in countries without animal welfare legislation and often no consideration is given to the needs of the animals in terms of cage environment, companionship etc. Due to the extensive use of reptile leather through all ages it is however not likely that the use of reptile leather will be banned due to extensive consumer demands.

In view of the above, it would be advantageous to be able to isolate cells for the production of reptile leather from already hatched reptile eggs by in vitro methods, thereby avoiding any ethical considerations regarding animal welfare and the killing of animals for the leather only. Further the number of animals raised and slaughtered in traditional farming may be reduced by using the isolated cells for scarless tissue regeneration in animals that sustain an injury on farms.

It has not previously been shown that cells for production of reptile leather has been isolated from hatched reptile eggs.

SUMMARY OF DISCLOSURE

It is the aim of the disclosure to isolate cells from already hatched reptile eggs thus avoiding all ethical issues regarding the traditional ways of obtaining starting material from either biopsies or animals slaughtered for the leather industry. In a main aspect the present disclosure relates to a method for isolating cells from the chorioallantois from a hatched reptile egg:

An in vitro method for obtaining cells for reptile leather production comprising the steps of:
  obtaining cells from a hatched reptile egg, and
  isolating and/or culturing keratinocytes, fibroblasts, melanocytes, stem cells, or precursor cells.

The cells are isolated from a hatched reptile egg where the live hatchling has already emerged. One source of cells inside a hatched reptile egg is the chorioallantois. Other possible sources of cells from hatched reptile eggs include the allantois, the allantoic sac, the amnion, the amniotic sac, the albumen, the yolk, and the yolk sac.

The stem cells may be dermal stem cells or mesenchymal stem cells.

The cells are isolated by culture in appropriate cell culture media where the cells can be kept in a stem cell or precursor cell state or differentiated into fibroblasts, keratinocytes, and melanocytes or any other cell type needed for in vitro production of reptile leather thus isolating the cells of the disclosure. Alternatively, as demonstrated in the examples, fibroblasts and keratinocytes can be obtained directly from the chorioallantois and be expanded into substantially pure cultures of these cells. It is expected that melanocytes can likewise be isolated from chorioallantois or be differentiated from precursor or stem cells.

Further, to avoid scar tissue formation the cells isolated from the hatched egg shell or the chorioallantois of a specific individual of reptile can be cryopreserved and used later for tissue regeneration of that specific individual in case of damage to the skin in a farming facility.

Another aspect of the present disclosure relates to a bioartificial reptile leather obtained or obtainable by the methods described herein above.

A further aspect of the present disclosure relates to an article of clothing or of leather goods comprising at least a portion which incorporates a bioartificial reptile leather obtained or obtainable by the method described herein above.

Yet an aspect of the present disclosure relates to the use of isolated keratinocytes, isolated dermal stem cells and mesenchymal stem cells, melanocytes, or immortalized fibroblast cells, obtained from a hatched reptile egg for in vitro production of a bioartificial reptile leather product.

Further isolated or differentiated fibroblasts, keratinocytes, and melanocytes can be grown in vitro for production of reptile collagen. Reptile collagen can be used to produce artificial reptile leather product according to methods described in WO2013149083, WO2014201406, and WO2017003999.

DETAILED DESCRIPTION OF THE DISCLOSURE

Figure 1:
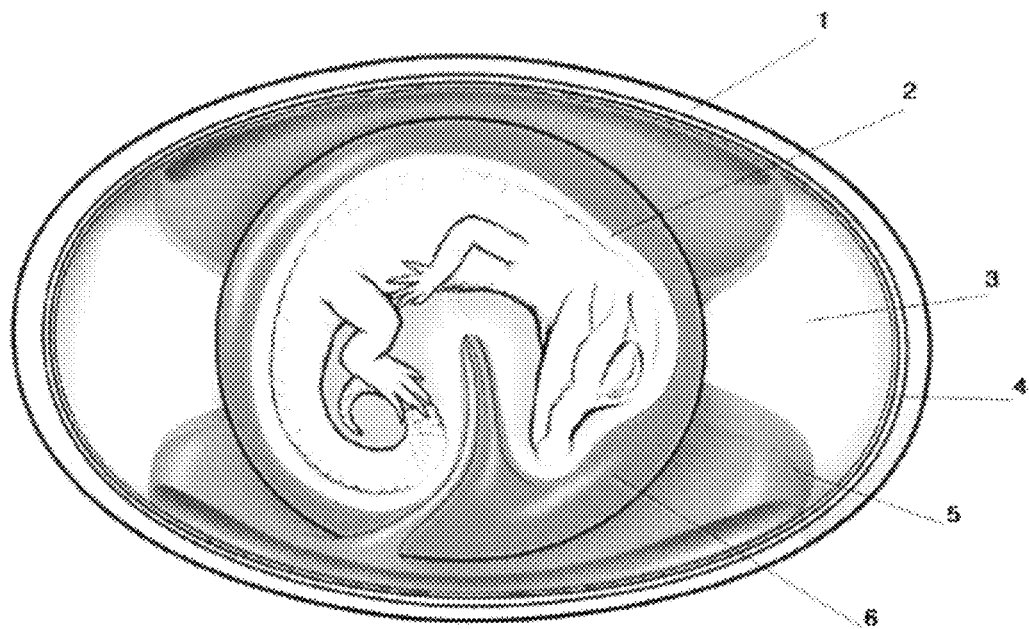
FIG. 1. Diagram of reptile egg. Source: (*Biology and evolution of crocodylians*, Gordon Grigg and David Kirshner, 2015).

Leather has always been an important source of material for humans in various applications such as clothing (e.g shoes, jackets, hats, bags, belts) for bookbinding and furniture covering due to its durability and flexibility. Especially reptile leather is considered a luxury item. However, there are many ethical issues regarding the killing of wild and/or farmed animals for their skins only.

The present disclosure relates to isolation of cells from hatched eggs from reptiles for artificial leather produced entirely by in vitro methods from cells obtained from a hatched reptile egg.

By a reptile is meant the traditional understanding of the term reptiles. According to this definition reptiles are those amniotes that lack fur or feathers. The group comprises today's (i.e. non-extinct) turtles, crocodilians, snakes, amphisbaenians, lizards, and *tuatara*. Examples of representative reptiles include turtles, tortoises, *Iguana*, agamas, chameleons, skinks, anoles, lizards, geckos, boas, anacondas, pythons, mambas, vipers, adders, rattlesnakes, crocodiles, alligators, and gavials.

The isolation of cells from hatched reptile eggs for production of bioartificial reptile leather has the advantage that no negative impact will be imposed on animals as opposed to e.g biopsies for isolating the required cells. The isolated cells can subsequently be used to produce bioartificial reptile leather using in vitro methods only and thereby avoiding any ethical issues relating to trapping and killing of wildlife for their skins only and animal welfare issues relating to conventional reptile farming. Another advantage of isolating cells from hatched reptile eggs is that cells can be isolated from endangered species without the risk of harm to individual animals and thereby the conservation of the species as a whole. Yet another advantage is that the isolation of cells from the chorioallantois from a specific reptile individual can be cryopreserved. The cells can subsequently be used in scarless tissue regeneration of the skin in animals sustaining skin injuries on farms. If scar tissue develops parts of the skin will have to be discarded and cannot be used in production of luxury items. With scarless tissue regeneration less skins will have to be discarded and thereby the number of animals used to produce a certain amount of luxury items could be reduced.

The cells isolated from the hatched reptile egg according to the disclosure may be used to produce artificial reptile leather that may be used in any way that reptile leather is traditionally used, such as for clothing, furniture, applications and accessories on clothing or furniture, and other reptile leather wear including home wear.

The cells isolated from the hatched reptile egg according to the present disclosure are preferably cells isolated from the vascularized chorioallantois obtained from a hatched egg from a reptile of choice. As described elsewhere, other parts of the hatched reptile egg may give rise to cells as well. The isolated cells are preferably keratinocytes, dermal stem cells, mesenchymal stem cells, melanocytes, or fibroblast cells. In addition the cells isolated in the present disclosure may be subsequently dedifferentiated and/or transdifferentiated from fibroblasts, keratinocytes, melanocytes etc. into cells exhibiting stem cell properties which subsequently can be (re-)differentiated into cells suitable for being used for in vitro reptile leather production or tissue regeneration.

Dedifferentiation and/or transdifferentiation (e.g. by means of Basic Fibroblast Growth Factor) of fibroblast cells and/or a fibroblast cell line into cells which exhibit stem cell properties such as progenitor cells may be performed after isolation of cells from the chorioallantois, Such progenitor cells may further be differentiated into cells suitable for in vitro production of reptile leather. Dedifferentiation and/or transdifferentiation of keratinocytes into their precursor cells may as well be used by the present disclosure. Dedifferentiation and/or transdifferentiation of the present disclosure may be reversine-mediated.

The isolation of cells of the present disclosure may be based on chorioallantois obtained from any reptile that may or may not presently be utilized for their leather such as *crocodilia* (alligators and crocodiles) *Chelonia* (tortoises and turtles) *Squamata* (lizards and snakes), and Rhynchocephalia (the *tuatara* or *Sphenodon puntatus*).

Method

In a main aspect the present disclosure relates to a method for isolating viable cells from a hatched reptile egg:
obtaining cells from a hatched reptile egg, and
isolating and/or culturing keratinocytes, fibroblasts, melanocytes, stem cells, or precursor cells.

FIG. 1 illustrates the different components of a reptile egg. Including the chorion, allantoic sac, amnion, amniotic sac, amniotic fluid, umbilical stalk, yolk sac and yolk.

Conspicuous and mostly at each end of the egg by mid-incubation, the albumen (3) provides a source of water, which becomes reduced to rubbery pads as development proceeds. Also conspicuous is the yolk, contained within the yolk sac (6) and the embryo developing within its amniotic sac (2). Less noticeably, the whole contents of the egg are surrounded by the membranous chorion (4). The embryo is nourished by the yolk via the vitelline artery and vein, which exit and enter the embryo via the umbilical stalk. This arrangement is reminiscent of the way in which developing placental mammals acquire nourishment from the maternal blood supply across the placenta. The allantois is a balloon like out-pocketing from the gut, which stores waste products. Early in development, gaseous ammonia is excreted but this is gradually replaced by urea, which is stored in the allantoic sac (5). The allantois, small at first, gradually expands until it envelops most of the egg contents. Fusing with the chorion where it is pressed against the external shell, it forms the chorioallantois, providing for $O_2$ and $CO_2$ exchange between the embryo and the atmosphere of the clutch cavity, via the shell and shell membranes. As the embryo's $O_2$ requirements increase the chorioallantois progressively increases in size, forming and expanding opaque band (1) around the equator of the egg. The gases are carried by the chorioallantoic artery and vein which exit and enter the embryo via the umbilical stalk. At the time of laying, the embryo, atop the yolk, is only a few millimetres in length and the egg contents are almost entirely yolk and albumen. As the embryo grows, these are consumed progressively, taking up less space as the volumes of both embryo and allantoic sac increase (*Biology and evolution of crocodylians*, Gordon Grigg and David Kirshner, 2015).

In an embodiment the cells of the present disclosure are isolated from chorioallantois from a hatched reptile egg. Other parts of the hatched egg may also give rise to cells.

In another embodiment the reptile as referred to in the present disclosure is an endangered species and/or selected from the group consisting of Crocodilian (alligators and crocodiles), *Chelonia* (tortoises and turtles), *Squamata* (lizards and snakes), and Rhyncocephalia (the *tuatara* or *Sphendon puntatus*)

According to the method of the present disclosure the cells are isolated from different individuals of a species of a reptile or, according to a preferred embodiment, the cells are isolated from a one and same individual of a species of a reptile.

In a preferred embodiment, the cells are not genetically modified.

In a preferred embodiment, the cells from the chorioallantois can be propagated and stored for later use, thus eliminating the need for sampling of hatched eggs for each production of bioartificial reptile leather. Further, cells from a hatched reptile egg may be stored as a source of donor cells for that individual, for example to repair damages to the animal's reptile skin.

Methods for Making Reptile Leather

Reptile leather in one embodiment may be produced by culturing fibroblasts, keratinocytes and melanocytes and growing the cells into a skin. In order to increase the strength of the skin or leather, the cells may be grown on a fibrous or mesh support. Further colorants may be added to make a reptile pattern to the skin. Methods for growing cells into a fiber or mesh reinforced leather are described in WO2016073453.

In another embodiment, isolated reptile fibroblasts, keratinocytes, and melanocytes are grown in vitro to produce collagen. The collagen can be harvested and be processed into an artificial reptile leather, for example by methods described in WO2013149083, WO2014201406, and WO2017003999.

Keratinocytes, Dermal Stem Cells, Mesenchymal Stem Cells, Melanocytes, and/or Immortalized Fibroblast Cells The stem cells such as dermal stem cells, and mesenchymal stem cells, keratinocytes, melanocytes and/or fibroblast cells, as described herein, can be isolated by culturing in cell specific media.

In one embodiment, the epidermal and dermal stem cells are isolated by culturing.

Keratinocytes may be isolated by culturing in conditioned CnT-prime epithelial culturing media (CellnTec) added 10% chelated FBS in TC treated cell culture plates with or without a feeder layer.

Fibroblasts may be isolated by culturing in CnT-prime fibroblast culturing media (CellnTec) in TC treated cell culture plates.

Mesenchymal stem cells may be isolated by culture in DMEM/F12 (1:1), 20 ng/mL EGF, 40 ng/mL bFGF, 2% B27 in non TC treated cell culture plates where cells form free floating spheres. Culturing can also be one on TC treated plates where cells attach to the culture plate and spheres are subsequently formed and released by the adherent cells.

Mesenchymal stem cells may differentiate into fibroblasts and keratinocytes, as well as other cell types according to methods known in the art. Differentiation of mesenchymal stem cells into fibroblasts may require addition of Connective tissue Growth Factor in growth media such as DMEM/F12, 2% B27, 20 µg/mL EGF, 40 µg/mL FGF.

Certain cells may be grown into substantially pure cultures by physically separating the cells during culture, for example by taking advantage of different degrees of attachment among cells and between cells and the surface they grow on.

Media

The table below provides a non-limiting list of media names and compositions which may be used for isolation and culturing according to the present disclosure.

| | | |
|---|---|---|
| Keratinocytes | Base media:<br>CnT-prime epithelial<br>culture medium | Proliferation media:<br>CnT-Prime epithelial<br>culturre media + 10%<br>chelated FBS. Media is<br>conditioned on reptile<br>fibroblasts for 1-5 days and<br>subsequently sterile filtered<br>using a 0.22 µM sterile<br>filter. |
| 3T3 Feeder cell<br>media | Culture media:<br>990 mL DMEM/F12 (3:1)<br>3.07 g Sodium Bicarbonate<br>0.475 g L-glutamine<br>10 mL 100x<br>Penicillin-Streptomycin | Mitomycin treatment:<br>Media is removed and cells<br>are washed 2× in PBS.<br>Cells are incubated in<br>DMEM with 15 µg/mL<br>Mitomycin for 2 hours at<br>37° C. Mitomycin is<br>removed and cells are<br>washed 2× in PBS. |
| Fibroblast<br>media | CnT-prime fibroblast<br>culture media | |
| Mensenchymal<br>cells | Propagation media<br>DMEM/F12<br>2% B27<br>20 ng/mL EGF<br>40 ng/mL FGF | Differentiation<br>DMEM/F12<br>2% B27<br>100 ng/mL cTGF |

Examples

Preparation of Mixed Cell Population from Chorioallantois

The chorioallantois was harvested from freshly hatched *Alligator mississippiensis* eggs according to the method previously described by Kjelland and Kreamer, Avian Biology Research 5(3), 2012.

Post-hatched eggs were sampled as soon as the reptile emerged by collecting the vascularized chorioallantois membrane from inside the egg using sterile forceps. To minimize bacterial contamination the chorioallantois was washed by transferring to a tube containing 25 mL DMEM/F12 1:1, 10% FBS, 50 µg/mL Gentamycin, 1% PSA (Penicillin streptamycin amphotericin B), 0.25 µg/mL Amphotericin B and swirled to wash. The washing procedure was repeated 3 times in total by transferring the chorioallantois to tubes with fresh washing media as described above.

The chorioallantois was then digested in 25 mL accutase for 30-60 min @31° C., and the tube is gently swirled every 5 min. The accutase was aspirated and transferred to a tube with CnT Prime epithelial culture media (CellnTech) containing 10% chelated FBS, 1% Penicillin/streptomycin/amphotericin B. Cell solution was strained serially through 100, 70, and 40 µM cell strainers. Cells were spun down @300×g for 10 min and supernatant removed. Cell pellet was resuspended in conditioned CnT Prime epithelial culture media (CellnTech) containing 10% chelated FBS, 1% Penicillin/streptomycin/amphotericin B. To avoid cell culture infection other antibiotics and antifungals can also be used i.e. gentamycin, nystatin.

A portion of the cells was at this point cryopreserved using 10% DMSO/20% FCS/70% conditioned CnT-prime, 10% FBS.

For isolation of keratinocytes the cell solution was plated on TC treated cell culture plates without feeder layer with conditioned CnT Prime epithelial culture media (CellnTech) containing 10% chelated FBS, 1% Penicillin/streptomycin/amphotericin B (PSA). Cell cultures were incubated @31° C., 5% $CO_2$.

Figure 2:
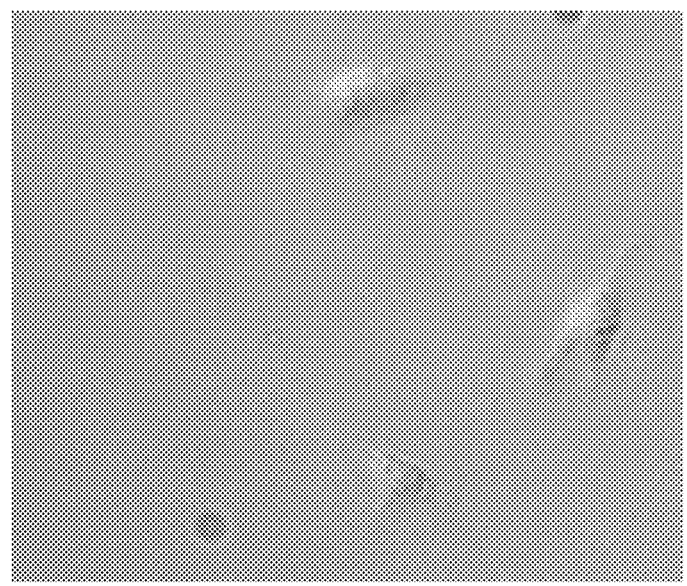
FIG. 2. Keratinocytes isolated from chorioallantois from reptile egg.

Cells appeared after 7-10 days, see FIG. 2 (species *Alligator mississippiensis*).

The accutase treated chorioallantois was transferred to a tube containing 25 mL DMEM with 0.2-1% collagenase I.

Tube was incubated at 31° C. overnight for digestion. The following day the tube was retrieved and the cell solution with the digested chorioallantois was added 25 mL DMEM/F12 (1:1), 10% FBS, 1% PSA. The cell solution was strained serially through 100, 70, and 40 µM cell strainers. Cells were spun down @300×g for 10 min and supernatant was removed.

A portion of cells was at this point cryopreserved (using 10% DMSO/20% FCS/70% cell specific media) without isolation of specific cell types and the rest of cells was set up for culture.

Figure 3:
FIG. 3. Fibroblast isolated from chorioallantois from reptile egg.

For isolation of fibroblasts cell the pellet was re-suspended in CnT-prime fibroblast culture media, 10% FBS, 1% PSA and plated on a TC treated cell culture dish. Cells were incubated @ 31° C., 5% CO2. FIG. 3 illustrates a fibroblast from *Alligator mississippiensis*.

During subsequent sub-culturing cells can be detached with trypsin or dispase leaving other more strongly adherent cell types still attached to the culture dish while fibroblasts will detach more quickly which will allow for a subculture with nearly 100% fibroblasts.

For isolation of mesenchymal stem cells, cell pellet is re-suspended in DMEM/F12 (1:1), 20 ng/mL EGF, 40 ng/mL bFGF, 2% B27, 1% PSA and plated on a non TC treated cell culture dish. Cells are incubated @ 31° C., 5% CO2. Mesenchymal stem cells will form spheres and proliferation occurs in sphereform and the cells can be isolated by removal of media with spheres and subsequent centrifugation. Elimination of some other cell types will be due to their adherence to the culture dish which is discarded after removal of media with spheres.

Testing for Presence of Mesenchymal Stem Cell Markers with Real-Time PCR

Cell Thawing

A frozen vial containing cell suspension from digested allantochorion from *Alligator Mississippiensis* (family: alligatoridae) as described above was thawed at room temperature (RT). Immediately upon being thawed, 1 mL of complete culture medium (Dulbeccos Modified Eagle Medium (DMEM; Euroclone, Italy)+10% heat inactivated Fetal Bovine Serum (FBS, EuroClone) and 1% Penicillin/Streptomycin (P/S; EuroClone) was taken from 31° C. and added slowly to the vial. Cells were transferred to a tube containing 5 mL complete medium.

The cells were centrifuged at 1200 rpm for 4 minutes at RT. Supernatant was removed, and 1 mL of Phosphate Buffered Saline (PBS; EuroClone) was added to and cells pellet was washed.

A cell count was done using a part of the cell suspension using a cell counter (Countess II, Thermo Fisher Scientific, Waltham, Mass., USA) with a result of 3.05×10e5 cells/mL. The remaining cells were centrifuged at 1200 rpm for 4 minutes at RT.

As Control a vial containing fibroblasts from a reptile belonging to the alligatoridae family was thawed using the same procedure as above. A cell count was performed for the fibroblast control sample resulting in 6.4×10e5 cells/mL.

Total RNA Isolation

Total RNA was isolated from control and test samples using the Total RNA purification kit (Norgen Biotek, Thorold, Canada) according to the manufacturers procedure. 350 µL of Buffer RL were added to the cell pellets, then transferred to a gDNA Removal Column assembled to a collection tube.

Lysates were centrifuged at 140000 rpm for 1 min at RT. The flow through was collected and added to 210 µL of absolute Ethanol and subsequently loaded on a RNA Purification Column assembled to a new collection tube. The solution was centrifuged at 6000 rpm for 1 min at RT.

Column was washed by adding 400 µL Wash Solution A to the column. Column was centrifuged for 1 min at 14000 rpm at RT. Washing step was repeated 3 times.

Total RNAs collected was diluted by adding 20 µL of Elution Solution A to each column and centrifuging for 2 min at 2000 rpm, followed by centrifuging for 14000 rpm for 1 min at room temperature.

RNA quality and concentration of the sample and control were measured using the NanoDrop™ ND-1000 (Thermo Fisher Scientific). Sample total RNA was measured to 187 ng/µL (260/280=1.95; 260/230=1.81). Control total RNA was measured to be 258.6 ng/µL (260/280=2.06; 260/230=1.91)

First-Strand cDNA Synthesis

The complementary DNA (cDNA) was synthesized following the SensiFAST™ cDNA Synthesis Kit (Bioline, Singapore). For Sample and Control, 500 ng of total RNA was retro-transcribed in a reaction volume of 20 µL. Each reaction contained 4 µL of 5× TransAmp Buffer, 1 µL of Reverse Transcriptase, and 15 µL of RNA (500 ng of RNA each for Sample and Control). Reaction was performed in the LifePro Thermal Cycler (Bioer Technology, China) using the following program: primer annealing for 10 min at 25° C., reverse transcription for 15 min at 42° C., and enzyme inactivation for 5 min at 85° C. Their resultant cDNA was stored at −20° C. until Real-Time PCR was performed.

Real-Time PCR

Real-time PCR was performed on a Rotor-Gene 3000 (Corbett Research, Sydney, Australia). A total of 1.5 µL cDNA was added to the final reaction volume of 15 µL. The reaction mixture consisted of 7.5 µL of 2× SensiFAST™ SYBR® No-ROX mix (Bioline), 1.2 µL each of 10 µM forward and reverse primer, and 3.6 µL of $H_2O$. The following PCR program was used: 95° C. for 2 minutes, followed by 45 cycles of 95° C. for 5 seconds, 60° C. for 10 seconds and 72° C. for 20 seconds. Sample and Control was tested for CD90 and CD166, well-characterized markers of stem cells of mesenchymal origin. Actin Beta was used as an internal reference to ensure identical starting conditions and for normalizing relative expression data.

The primer sequences used were: CD90 Forward primer: AGCAAGGACGAGGG-CACCTACA, Reverse Primer: TGGGAGGAGATGGGTGGGGAAT, CD166 Forward primer: TCAAGGTGTTCAAGCAACCA Reverse Primer: CTGAAATGCAGTCAC-CCAAC, Actin Beta Forward primer: TGGTGGGCATGGGTCAGAAGGA, Reverse Primer: ATGCCGTGCTCGATGGGGTACT.

For the quantification of mRNA transcription, the relative 2ΔΔCt method was used [Pfaffl]. Relative quantification is commonly used to compare the expression levels of a gene in different samples. When studying gene expression, the quantity of the target gene transcript needs to be normalized against variation in sample quality and quantity between samples. To ensure identical starting conditions, the relative expression data were normalized using Actin Beta (ACTB) as internal reference.

Figure 4:
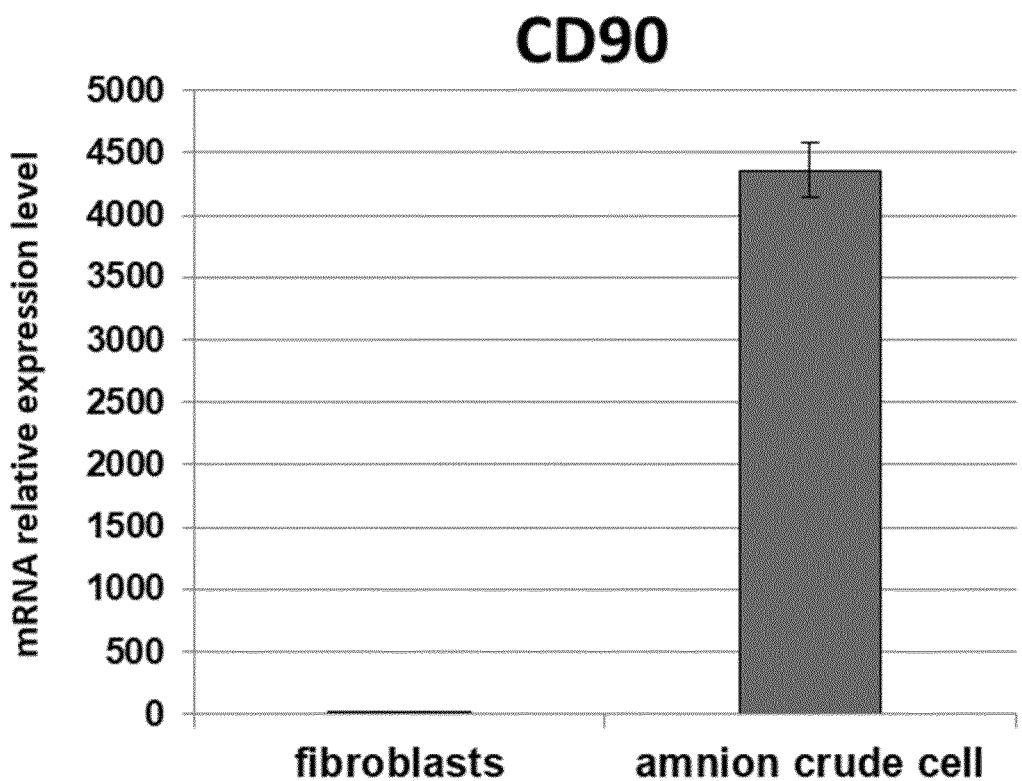
FIG. 4. Real-Time PCR showing high expression of stem cell marker CD90 in cells isolated from chorioallantois from reptile egg.
Figure 5:
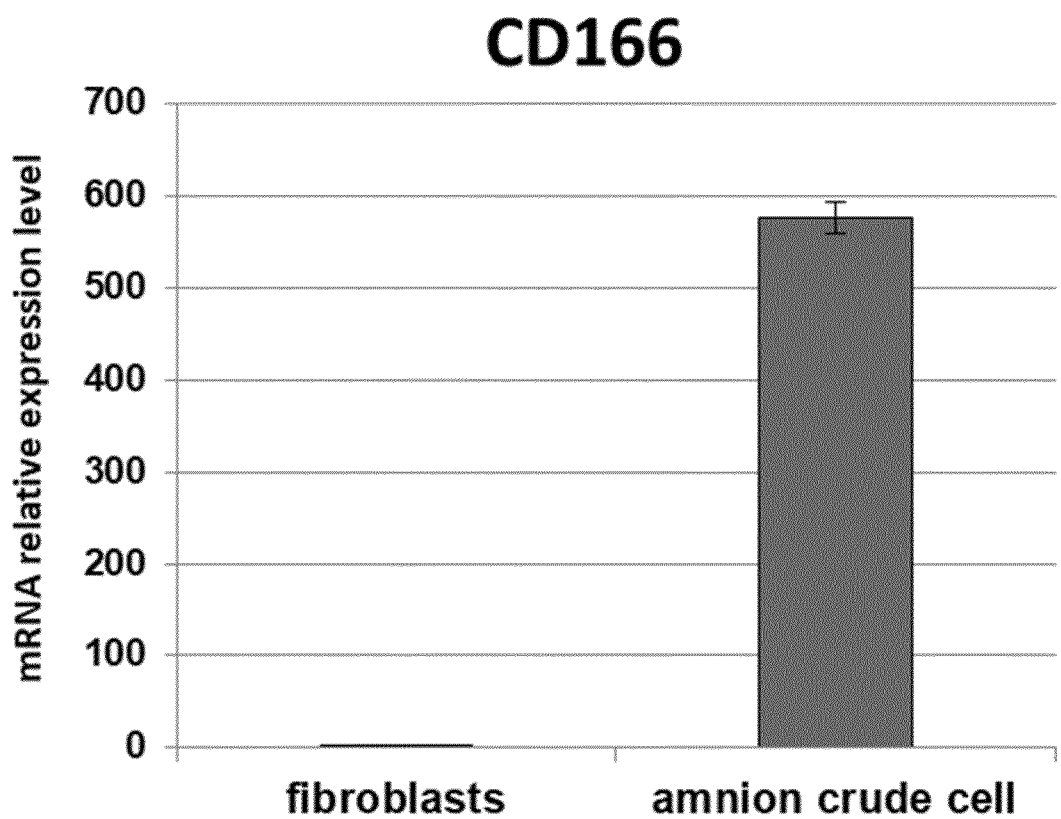
FIG. 5. Real-Time PCR showing high expression of stem cell marker CD166 in cells isolated from chorioallantois from reptile egg.

The results show that the relative expression of CD90, also known as THY1, was approximately 4300× higher compared to Control (fibroblasts) and to house keeping gene Actin Beta (FIG. 4) and the relative expression of CD166, also known as ALCAM, was approximately 580× higher compared to Control (fibroblasts) and to house keeping gene Actin Beta. (FIG. 5), proving presence of stem cells of mesenchymal origin.

REFERENCES

Kjelland et Kraemer, Avian Biologiy Research 5 (3), 2012
Chang et al, Int J Dev Biol. 2009; 53(5-6): 813-826
Pfaffl, M W. A new mathematical model for relative quantification in real-time RT-PCR. Nucleic Acids Res. 2001; 29(9):e45.

The invention claimed is:

1. An in vitro method for obtaining cells for reptile leather production comprising the steps of:
    (a) obtaining cells from a hatched reptile egg from which a reptile has emerged, wherein said cells comprise one or more of keratinocytes, fibroblasts, melanocytes, stem cells, or precursor cells, and wherein said cells are not obtained from the reptile that has emerged; and
    (b) isolating and/or culturing the cells obtained in (a) which comprise one or more of keratinocytes, fibroblasts, melanocytes, stem cells, or precursor cells.

2. The method of claim 1, wherein the cells are isolated by the use of surface markers.

3. The method of claim 1, wherein said cells are isolated by flow cytometry, such as by fluorescence-activated cell sorting (FACS).

4. The method of claim 1, wherein the cells are isolated by culturing a mixed culture of cells in cell specific media to obtain substantially pure cultures of specific cell types.

5. The method of claim 1, wherein substantially pure culture of one of the cell types is obtained by physically separating cells of one type from other cells, e.g. through trypsination.

6. The method of claim 5, wherein fibroblasts are differentiated from mesenchymal stem cells.

7. The method of claim 1, wherein cells are isolated from the chorioallantois.

8. The method of claim 1, wherein cells are isolated form the allantois, the allantoic sac, the amnion, the amniotic sac, the albumen, the yolk, or the yolk sac.

9. The method of claim 1, wherein epidermal and dermal stem cells, mesenchymal stem cells, melanocytes and/or fibroblast cells are isolated by culturing in cell specific media.

10. The method of claim 1, wherein keratinocytes, fibroblasts, or melanocytes are obtained by differentiation of stem cells or precursor cells.

11. The method of claim 1, wherein the cells are cultured in presence of at least one growth factor.

12. The method of claim 1, wherein the cells are cultured in presence of fibroblast growth factor, epidermal growth factor, and/or connective tissue growth factor.

13. The method of claim 1, wherein cells are cultured on a layer of feeder cells.

14. The method of claim 1, wherein the cells are not genetically modified.

15. The method of claim 1, comprising obtaining substantially pure cultures of keratinocytes, fibroblasts, and melanocytes.

16. The method of claim 1, wherein cultures of one or more of the cell types are cryopreserved.

17. The method of claim 1, wherein keratinocytes, fibroblasts, and melanocytes are obtained from one species.

18. The method of claim 1, wherein keratinocytes, fibroblasts, melanocytes are obtained from the same egg.

19. The method of claim 1, wherein different cell types are isolated from different eggs of the same species.

20. The method of claim 1, wherein different cell types are isolated from different eggs of different species.

21. The method of claim 1, wherein the reptile is selected from *crocodilia* (alligators and crocodiles), *Chelonia* (tortoises and turtles), amphisbaenians, *Squamata* (lizards and snakes), and Rhynchocephalia (the *tuatara* or *Sphenodon puntatus*).

22. The method of claim 1, wherein the reptile is selected from snake, *Alligator*, crocodile, *tuatara*, turtles, tortoises, *Iguana*, agamas, chameleons, skinks, anoles, lizards, geckos, boas, anacondas, pythons, mambas, vipers, adders, rattlesnakes, crocodiles, alligators, and gavials.

23. The method of claim 1, further comprising growing a mixed culture of keratinocytes, fibroblasts, and melanocytes into a bioartificial reptile leather.

24. The method of claim 23, wherein the cells are cultured on a support, which comprises at least one of a fibre support and a mesh support.

25. The method of claim 1, further comprising transplanting a mixed culture of keratinocytes, fibroblasts, and melanocytes to a reptile for skin repair.

26. The method of claim 1, further comprising culturing keratinocytes, fibroblasts, and/or melanocytes and harvesting reptile collagen from said cells.

27. The method of claim 26, further comprising producing artificial reptile leather from said harvested collagen.

* * * * *